(12) United States Patent
Rathke et al.

(10) Patent No.: US 6,968,247 B2
(45) Date of Patent: Nov. 22, 2005

(54) METHOD AND APPARATUS FOR PRODUCING A DENTAL PRODUCT

(75) Inventors: Andreas Rathke, Schaan (LI); Andreas Reindl, Batschuns (AT); Frank M. Kretschmar, Lindau (DE); Diethard Bertsch, Gofis (AT)

(73) Assignee: Ivoclar Vivadent AG, Schaan (LI)

( * ) Notice: Subject to any disclaimer, the term of this patent is extended or adjusted under 35 U.S.C. 154(b) by 50 days.

(21) Appl. No.: 10/396,865

(22) Filed: Mar. 25, 2003

(65) Prior Publication Data

US 2004/0143351 A1 Jul. 22, 2004

(30) Foreign Application Priority Data

Jan. 17, 2003 (DE) .................... 103 01 643

(51) Int. Cl.[7] ................ G06F 19/00; A61C 13/34
(52) U.S. Cl. ............... 700/98; 433/213; 700/163; 700/182; 702/182
(58) Field of Search ............. 700/98, 108, 109, 700/117, 118, 163, 174, 179, 182, 195; 702/84, 702/182; 433/213, 229

(56) References Cited

U.S. PATENT DOCUMENTS

| | | | |
|---|---|---|---|
| 4,478,580 A | | 10/1984 | Barrut |
| 5,452,219 A | * | 9/1995 | Dehoff et al. .............. 700/163 |
| 6,579,095 B2 | * | 6/2003 | Marshall et al. ........... 433/213 |
| 6,772,026 B2 | * | 8/2004 | Bradbury et al. ............ 700/98 |
| 6,832,877 B2 | * | 12/2004 | Hamada .................... 409/96 |
| 2002/0007294 A1 | * | 1/2002 | Bradbury et al. ............ 705/7 |
| 2003/0123943 A1 | * | 7/2003 | Hamada .................... 409/96 |
| 2004/0133293 A1 | * | 7/2004 | Durbin et al. ............... 700/98 |

FOREIGN PATENT DOCUMENTS

| | | |
|---|---|---|
| AU | 200040840 B2 | 1/2001 |
| DE | 199 22 870 A1 | 12/2000 |
| DE | 102 03 665 A1 | 11/2002 |
| EP | 1 062 916 A2 | 12/2000 |
| EP | 1 088 526 A2 | 4/2001 |
| WO | WO 01/37757 A1 | 5/2001 |

OTHER PUBLICATIONS

H. Rudolph et al, "Innovative test for internal and occlusal fit of CAD/CAM-fabricated restorations"; Dtsch. Zahnartz. Z. 57 (2002) pp. 540-545; Cologne, Germany.

* cited by examiner

*Primary Examiner*—Paul Rodriguez
(74) *Attorney, Agent, or Firm*—John C. Thompson; Alan S. Korman

(57) ABSTRACT

A stock removal workshop for the production of a dental restoration product includes a stock removal machine operable to remove stock material from a blank such that there remains a dental product having the desired geometry requisitioned by a dental practice or a dental laboratory. A stock removal plotter controls the stock removal machine operation and converts requisition data received from the dental practice or the dental laboratory which characterizes a virtual model of the requisitioned dental product into control data for controlling the stock removal machine operation. A geometry following assembly characterizes the geometry of the produced dental product via a geometry following operation and a comparison device compares the geometry characterizing data relating to the produced dental product with the requisition data to determine deviations therebetween.

19 Claims, 1 Drawing Sheet

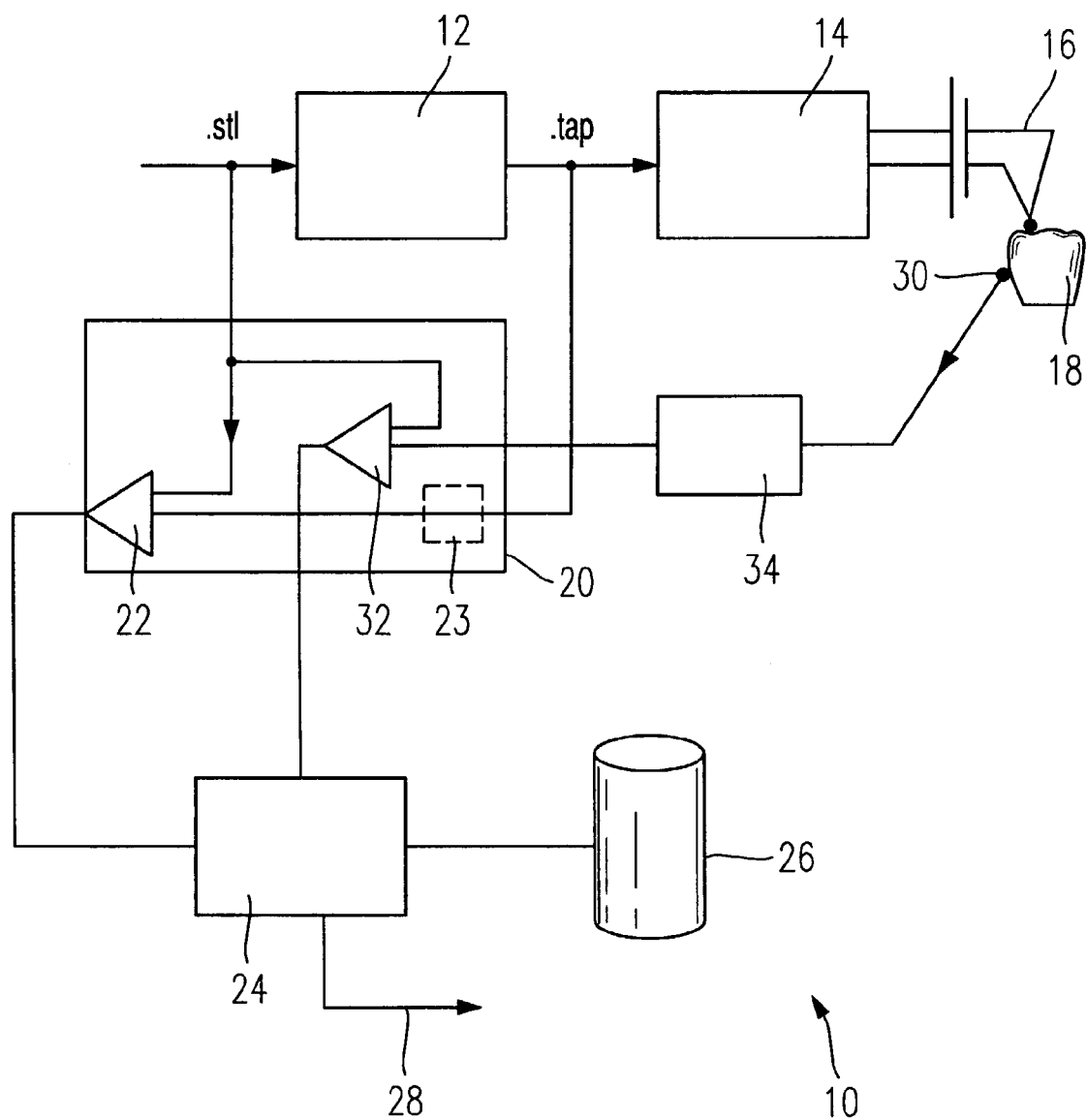

METHOD AND APPARATUS FOR PRODUCING A DENTAL PRODUCT

CROSS-REFERENCE TO RELATED APPLICATIONS

This application claims foreign priority benefits under 35 U.S.C. §119(a)-(d) from German patent application ser. no. P 103 01 643.0 filed Jan. 17, 2003.

TECHNICAL FIELD

The present invention relates to a method for producing a dental product, especially, a dental restoration, as well as a dental restoration apparatus, a stock removal method and a stock removal apparatus.

BACKGROUND OF THE INVENTION

It has long been known to deploy dental restoration methods and dental restoration apparatus to produce, based upon predetermined data, dental products. Such production is typically effected via a stock removal device which, as a rule, removes stock material from a blank such that there remains a dental product having the desired geometry wherein, preferably, the desired stock material removal work is effected via milling or grinding.

For some time, numerically controlled stock removal processes have been deployed, as well, in the dental field in order to achieve as precise a restoration result as possible. In this connection, a virtual restoration is produced in a dental laboratory, based upon information provided from a dental practice which can, for example, encompass imprint information of the jaw or mandible of the respective patient, and information characterizing the virtual restoration is transmitted as a data packet to a stock removal workshop. Since the requisite stock removal effort in the stock removal workshop domain is not inconsiderable, it is advantageous if several dental laboratories transmit their data to the same stock removal workshop, whereupon the collective stock removal work is undertaken at that location.

On the other hand, it is known that each stock removal machine should be monitored in order to prevent the occurrence of defective parts. This monitoring can be effected by, for example, a simple monitoring device which can monitor the course of the production process in its entirety and can indicate via an alarm to a service person in the stock removal workshop if a defect occurs.

In fact, precisely as a result of the data transmission by several dental laboratories to a single stock removal workshop, the respective stock removal workshop is faced with the problem of determining which type of requisition data from the dental laboratories should be provided to it. Notwithstanding the specification of the particular type of requisition data to be sent, however, small differences between the requisition data can occur, depending upon the respective program that a dental laboratory uses. Most typically, such differences come about by the actions of the dental laboratory such as, for example, when sensing the geometry of a model as a step in the production of a virtual restoration, the dental laboratory program user determines how many measurement points should be taken into account. Typically, triangulated surfaces are surveyed and data relating thereto is provided as requisition data. For this reason alone, if there is variation in the mesh width of the grid of the triangulated surfaces, considerable differences occur among the requisition data and the requisition data must be differently interpreted if, for example, the mesh width of the grid decreases in a critical area of the restoration.

With regard to the stock removal plotter, which determines the necessary stock removal machine activities to remove stock material from a respective blank and which, from the requisition data, generates control data that is machine readable for controlling the stock removal activities of the stock removal machine(s), it is necessary by reason alone of the complex work process necessarily undertaken by the stock removal plotter that the restoration result—namely, the finished dental product—be subjected to a quality control overview.

A further problem in connection with the work set up of a stock removal workshop which services several dental laboratories is that of ensuring the proper association of each requisitioned product to the respective requisitioning laboratory. It is conventionally known to use a so-called invoicing program to provide an appropriate requisition work flow and, as well, to generate the invoicing. The reliability of such systems is, however, strongly dependent upon how completely the relevant requisition information has been inputted; to avoid defects, it is typically necessary that an additional work colleague be occupied with the quality control overview within the scope of the stock removal workshop activities.

Additionally, even if modern stock removal machines comprise an integrated monitoring device which senses the wearing out of the work tools that perform the stock removal, and which, optionally, senses the induced oscillations in connection with the stock removal work, and provides warning signals as a function of the sensing, a visual verification of the finished dental product is required in order to preclude the possibility that internal machine controls are operating in a defective manner.

Since the stock removal work in the stock removal workshop which services several dental laboratories is, due to the above-noted reasons, heavily plagued with defect occurrences or necessitates numerous special measures to combat the occurrence of such defects, it has also been recommended that a simple stock removal workshop be installed in the dental laboratory itself. Due to cost reasons, only relatively large dental laboratories can contemplate this type of configuration. Also, in this connection, the cost frameworks impose tight limits on the operation so that resort must be had to only the most cost effective machines.

In connection with the concept of a stock removal workshop, it is to be understood that this concept comprehends a station with a stock removal plotter and a stock removal device, wherein the station can preferably be provided with the corresponding requisition data and which can produce the dental product, independently of whether the station is remote from the requisitioning dental laboratory or is deployed in this laboratory.

OBJECTS AND SUMMARY OF THE INVENTION

In contrast to the above-noted conventional approaches, the present invention provides a solution to the challenge of providing a method for producing a dental product, especially, a dental restoration, as well as the challenge of providing a dental restoration apparatus and the associated stock removal process and apparatus all of which operate efficiently but which, nonetheless, offer a high acceptance rate in connection with dental laboratories.

Surprisingly, the methods and apparatus of the present invention permit the dental products to be reliably produced with a substantially improved quality standard and, by reason of the configuration of the inventive quality control device, a quality control monitoring of the requisition fulfillment work is possible. Even with such quality control capability, however, no or virtually no, additional costs are required, as the quality control device can make use of the already available stock removal plotter in order to implement the quality control function.

In a first embodiment of the inventive solution, the quality control device verifies the data produced by the stock removal plotter and compares such data with the requisition data. Also, in connection with this solution, a requisition quality control function can already be implemented in that the respective stock removal operation requisition can be associated with the requisitioning dental laboratory and it can be ensured via, for example, a numerical identification or a print identification, both that the predetermined deadlines are maintained and that the respective dental product is prepared for delivery to the requisitioning dental laboratory or, as well, that the invoicing is directed in the appropriate manner.

A further embodiment of the present invention permits an even more extensive level of quality control of the dental product to be achieved. The stock removal machine is provided with an optical or mechanical geometry scriber in lieu of the work tool, the geometry scriber being either automatic or manual, as desired, and being operable to follow the geometry of a produced dental product for the purpose of generating geometry characterizing operation data. The geometry scriber verifies the form of the produced dental product. The geometry characterizing operation (scanned) data are compared, in the quality control device, with the control data and/or with the requisition data so that it can be ensured that a defective dental product is not produced by virtue of the inputting of defective stock removal information.

It is especially advantageous, in connection with this further (second) embodiment, that the dental product can remain in the same position during this verification as it is in during the stock removal operation thereon. The availability of reference coordinates is considerably facilitated in this regard so that additional sources of defects are foreclosed. This solution is, above all, to be taken into account if the scanning process is substantially shorter than the stock removal process.

In a third embodiment of the present invention, the dental product is removed from the stock removal machine and is scanned and the scanned data are conducted to the quality control device for comparison thereat with other data.

It is to be understood that the inventive geometry characterizing operation is not limited to a mechanical geometry characterizing operation. Rather, in connection with the embodiment of the present invention wherein the scanning is performed on the dental product while still at the stock removal machine position, the work tool head is exchanged out for a scanning head, which offers the possibility of optical scanning.

It is, additionally, especially advantageous if the quality control scanner delivers the data in the same format as the data provided by the respective scanner deployed with regard to the virtual restoration generated by the dental laboratory or the dental practice. Data of the same type can even be deployed in order to maintain the tolerances as low as possible. The data are typically presented as ASCII data of a scatter plot, whereby the markings of the preparation limits are used as the reference points. It is to be understood, however, that other desirable suitable measures for producing the references can be deployed. The scanned data can either be compared as raw data or compared as enhanced or normalized data, and it is possible to have the gratings or rasters approximate one another to such an extent that raster defects are foreclosed. Other data, however, can be produced from the scatter plot such as, for example, .stl data produced via triangulation, and it is to be understood that this .stl requisition data can also be subjected to a comparison step.

It is significant that, in any event, in accordance with the present invention, the requisition data is produced independently from the output data of the scanner or geometry scriber so that a genuine quality control operation is possible. It is also possible to send or transmit back the comparison data together with the dental product to the requisitioning dental laboratory in order, at the same time, to present an example of the quality and the successful quality control measures.

In yet a further additional embodiment, it is possible to couple the scanner or the geometry scriber with the stock removal device such that a special software makes possible a length-independent positioning of the restoration in the scanner.

In connection with the inventive solution, it can additionally be foreclosed that dental products are delivered having a wavy surface produced by oscillations during the stock removal process. In order to avoid this occurrence, it has heretofore been the case that a comparatively low operational speed has been undertaken during the stock removal process. The higher the operational speed and the removal of material per unit time, the more likely it is, in connection with the stock removal process, that the process will lead to an oscillation or, on occasion, to a breakage of the blank. In accordance with the present invention, the stock material removal speed can be increased and, via the inventive quality control device, it is nonetheless ensured that solely intact or sound dental products are produced for delivery. Surprisingly, via exploitation of this approach, the cycle time for the production of a dental product is, in total, in fact reduced although the additional geometry characterizing operation step is undertaken. Also, in connection with cost factors, an increase of the scrap rate from, for example, 0.1 to 1% need not be taken into account, for all practical purposes, since the usage of the available stock removal device and, as well, of the entire stock removal workshop, are improved and, as a consequence thereof, are operated in an enhanced revenue producing manner.

The quality norms specified by ISO 9000 et seq can be realized, in connection with the present invention, since a comparison between the requisitioned product properties and the finished product properties is possible. The confidence which the quality control engenders in the dental laboratory, which is the customer, and in the stock removal work shop, is substantially greater, if, in addition to the finished product, the geometry characterizing operation data used for the quality control verification is sent as well to the dental laboratory.

Further advantages, details, and features of the present invention are set forth in the following description of an embodiment of the present invention with reference to the figures of the drawings.

BRIEF DESCRIPTION OF THE FIGURES

The sole FIGURE of the drawing is a schematic view of an inventive stock removal device for performing the inventive stock removal method of the present invention.

DETAILED DESCRIPTION OF THE PREFERRED EMBODIMENT

As shown in the sole FIGURE of the drawings, a stock removal workshop or center 10 comprises a stock removal plotter 12 which, in a conventional manner, produces control data for controlling the operation of at least one stock removal machine based upon requisition data provided by the party requisitioning the dental product work. The operations of stock removal machines are controlled with the control data, whereby, in the illustrated embodiment, solely one stock removal machine 14 is illustrated although, in practice, several stock removal machines such as, for example, four, or even eight, stock removal machines can be deployed as the respective stock removal devices.

The stock removal machines are configured in a conventional manner. They may be numerically controlled (NC) milling machines. Such machines typically comprises a five- or six-axis control of a tool 16, wherein the tool, supplied from a not-illustrated tool supply, can be controllably handled, removed, and deployed by the stock removal machine 14.

The stock removal machine 14 produces, in a conventional manner, a dental product 18 from a blank with the dental product being of a quality and having a geometry conforming respectively to the quality and geometry as have been stipulated by the requisition data.

The requisition data are delivered from a not-illustrated dental laboratory via transfer thereof along a remote data transfer connection, transfer thereof onto a diskette, or burning thereof onto a CD. In accordance with the present invention, it is provided that the respective dental technical laboratory requisition data are provided with a characteristic or marker in connection with their delivery which permits a unique identification of the laboratory.

In accordance with the present invention, a quality control device 20 is provided which makes possible the provision of feedback during and/or after the stock removal operation in the stock removal workshop. The quality control device 20 comprises a first comparison device 22 which, at the least, compares the control data with the requisition data.

The comparison can, for example, be effected via a corresponding conversion so that the stock removal plotter is subjected to a quality control function.

It is to be understood that the requisition data cannot be immediately compared with the control data, as each set of data is in a different data format than the other. Accordingly, the comparison can, on the one hand, be effected such that the control data are converted into requisition data, so that the comparison of the twice-converted requisition data (i.e., the requisition data initially converted into control data format and thereafter re-converted into requisition data format for comparison purposes) with the original requisition data can be undertaken. On the other hand, it is also possible to undertake, on the input side, a data transformation or conversion of the requisition data which can then, in a practical manner, be subjected to a quality control verification by the stock removal plotter 12.

A suitable data transformation or conversion device is shown in the sole FIGURE of the drawing in broken lines and is designated with the reference character 23.

The comparison result is transmitted to an evaluation device 24 which evaluates the comparison result in a suitable manner. For example, the comparison result can be displayed and an alarm can be activated if a deviation occurs. The documented work process can be continuously stored via a storage device 26 which permits conclusions to be drawn concerning the workload and quality of the work process in the stock removal workshop. Also, it is possible to transmit the evaluation data from the evaluation device to the respective dental laboratory so that a pre-work commencement packet of information is available in the event that the requisition request needs to be modified. This transmittal can occur via a data connector 28 which is also synchronized with the data connector which delivers the requisition data.

In a further embodiment of the present invention, a geometry scriber 30 is provided which can be, as required, under the control of the stock removal machine 14, the geometry scriber operating as desired in a continuous manner or at the conclusion of the milling or other work to characterize the contour of the dental product 18. The data which have been obtained by the scanning in of such data in this manner are transmitted to the quality control device 20 which comprises a further comparison device 32 that compares the scanned data either with the requisition data or with the control data. In the illustrated embodiment, a converter 34 is provided which prepares the data for transmittal of the scanned data to the quality control device 20.

The data which are evaluated by the comparison device 32 can, in any event, be transmitted to the evaluation device 24 which can also evaluate the data.

It is to be understood that, in lieu of the configuration of the quality control device as a combination device with the comparison device provided in combination with the quality control device, one of the comparison devices 22 and 32 can be omitted. In any event, in accordance with the present invention, feedback characterizing the work process results is provided, which permits the provision of further feedback to the dental laboratory.

The present invention is, of course, in no way restricted to the specific disclosure of the specification and drawings, but also encompasses any modifications within the scope of the appended claims. In this regard, the term "means for" as used in the claims is intended to include not only the embodiment illustrated in the drawing of this application and the equivalent designs discussed in the text, but it is also intended to cover other equivalents now known to those skilled in the art, or those equivalents which may become known to those skilled in the art in the future.

What is claimed is:

1. A method for producing a dental product, including a dental restoration, comprising the steps of:

receiving a requisition data packet at a stock removal workshop having at least one stock removal machine operable to remove stock material from a blank such that there remains a dental product having a desired geometry requisitioned by a selected one of a dental practice and a dental laboratory, the requisition data packet having a data format characterizing a geometry of at least one of a casting representing the dental product and a model representing the dental product, wherein the geometry characterizing data has been generated by a geometry following operation which generates data points characterizing the geometry of the respective one of the casting and the model, the geometry following operation including a selected one of scanning the respective one of the casting and the model and non-scanning following of the geometry of the respective one of the casting and the model, and wherein a geometry following operation on the dental product occurs while the dental product is still retained in its stock removal position at the stock removal machine;

converting the requisition data of the requisition data packet into control data for controlling at least one stock removal machine operation;

transmitting the control data to a stock removal machine;

producing the dental product having a finish geometry for eventual transmission thereof, following a monitoring of the dental product to insure that it is of a quality conforming to the selected one of the dental practice and the dental laboratory; and conducting a quality control activity on the produced dental product including producing a finished product data packet relating to the dental product in the data format of the requisition data following the production of the dental product and performing a data comparison between the requisition data and the finished product data packet and undertaking a selected one of further monitoring the quality of the dental product via at least one of the activities of a.) verifying the conformation of the dental product to at least one of the respective one of the casting and the model, b.) customizing the dental product via color conformation thereof with respect to its ultimate location, and c.) transmitting the dental product to the dental practice that will place the dental product in its ultimate location thereof for the purpose of determining the suitability of the dental product with respect to compatibility with surrounding structure after placement, and appearance, and not performing any of the further quality monitoring activities a.), b.) and c.).

2. A method according to claim 1, wherein receiving a requisition data packet includes having scanned data characterizing the geometry of a physical model of the dental product, which data is derived from scanning the physical model of the dental product to thereby derive a virtual model of the dental product; and transmitting the data packet relating to the virtual model to the stock removal workshop.

3. A method according to claim 1, and further comprising characterizing the geometry of the produced dental product via the geometry following operation in which the geometry of the produced dental product is followed via a selected one of scanning the produced dental product and non-scanning following of the geometry of the produced dental product in the stock removal workshop and determining, prior to the geometry following operation, tolerance values and rejecting as unacceptable the dental product in the event that a comparison device determines that such tolerance values have been exceeded.

4. A method according to claim 3, wherein, in connection with the geometry following operation on the produced dental product in the stock removal workshop, data is produced in a format which corresponds to the format of the requisition data.

5. A method according to claim 3, further comprising a selected one of exchanging out a stock removal tool of at least one stock removal machine for a selected one of an optical or mechanical geometry scriber and not exchanging out the tool.

6. A method for producing a dental product, including a dental restoration, comprising the steps of:

at a stock removal workshop having at least one stock removal machine operable to remove stock material from a blank such that there remains a dental product having a desired geometry requisitioned by a selected one of a dental practice or a dental laboratory, converting, via a stock removal plotter that controls at least one stock removal machine operation, requisition data received from the selected one of the dental practice and the dental laboratory which characterizes a virtual model of the requisitioned dental product into control data for controlling the stock removal machine operation;

after a stock removal operation to produce a dental product having a finish geometry, characterizing the finished geometry of the produced dental product via a geometry following operation in which data is generated as the geometry of the produced dental product is followed via a selected one of scanning the produced dental product and non-scanning following of the geometry of the produced dental product in the stock removal workshop, wherein the geometry following operation on the dental product occurs while the dental product is still retained in its stock removal position at the stock removal machine; and comparing the geometry characterizing data relating to the produced dental product with the virtual model to determine deviations therebetween.

7. A stock removal workshop for the production of a dental product, including a dental restoration product, comprising:

at least one stock removal machine operable to remove stock material from a blank such that there remains a produced dental product having a desired geometry requisitioned by a selected one of a dental practice and a dental laboratory;

a stock removal plotter for controlling the stock removal machine operation and operable to convert requisition data received from the selected one of the dental practice and the dental laboratory which characterizes a virtual model of the requisitioned dental product into control data for controlling the stock removal machine operation;

a geometry following assembly for characterizing the geometry of the produced dental product via a geometry following operation in which the geometry of the produced dental product is followed via a selected one of scanning the produced dental product and non-scanning following of the geometry of the produced dental product in the stock removal workshop, wherein the geometry following operation on the dental product occurs while the dental product is still retained in its stock removal position at the stock removal machine; and a comparison device connected to the geometry following assembly for receiving therefrom geometry characterizing data relating to the produced dental product and operable to compare the geometry characterizing data relating to the produced dental product with the virtual model to determine deviations therebetween.

8. A method for producing a dental product, including a dental restoration, comprising the steps of:

at a stock removal workshop having at least one stock removal machine operable to remove stock material from a blank such that there remains a dental product having a desired geometry requisitioned by a selected one of a dental practice and a dental laboratory, converting, via a stock removal plotter that controls at least one stock removal machine operation, requisition data received from the selected one of the dental practice and the dental laboratory which characterizes the desired geometry of the requisitioned dental product into control data for controlling the stock removal machine operation;

after a stock removal operation to produce a dental product having a finished geometry, characterizing the finished geometry of the produced dental product via a geometry following operation in which data is generated as the geometry of the produced dental product is followed via a selected one of scanning the produced dental product and non-scanning following of the geometry of the produced dental product in the stock removal workshop, wherein the geometry following operation on the dental product occurs while the dental product is still retained in its stock removal position at the stock removal machine; and comparing, via a quality control device connected to the stock removal plotter and having a comparison device, the geometry characterizing data relating to the produced dental product with the requisition data characterizing the geometry of the requisitioned dental product to determine deviations therebetween.

9. A method according to claim 8, wherein the data provided by the stock removal plotter to the quality control device are control data for controlling the stock removal machine operation and the quality control device compares the control data with the requisition data.

10. A method according to claim 8, wherein the data provided by the stock removal plotter to the quality control device are scanned data generated by scanning of the produced dental product, wherein the scanned data are influenced by the stock removal work performed on a blank by the stock removal machines to produce the produced dental product.

11. A method according to claim 8, and further comprising monitoring, via the quality control device, the fulfillment completion of a requisitioned dental product and providing feedback information relating thereto.

12. A method according to claim 8, and further comprising converting, via the stock removal plotter, the requisition data into point coordinates via triangulation into triangulated surfaces and, in connection with the geometry following operation on the produced dental product, converting point coordinates via triangulation into triangulated surfaces and comparing, via the quality control device, the requisition data with geometry characterizing data.

13. A method according to claim 8, wherein the geometry following operation on the produced dental product is effected within the stock removal workshop and, in particular, is effected via a non-scanning geometry characterizing operation.

14. A method according to claim 8, and further comprising continuously monitoring, via the quality control device, at least one stock removal machine and de-activating the at least one stock removal machine upon an occurrence of oscillations whose amplitudes exceed a pre-determined value.

15. A method according to claim 8, wherein the stock removal plotter controls a selected group of two through ten stock removal machines and, especially, a group of four stock removal machines.

16. A method according to claim 8, wherein the stock removal workshop is in data transmitting connection with one or more dental laboratories via remote data transfer connections and receives the requisition data from the dental laboratories.

17. A method according to claim 8, wherein the geometry following operation on the produced dental product includes exchanging out a tool of at least one stock removal machine for a selected one of an optical or mechanical geometry scriber operable to perform the geometry following operation on the dental product.

18. A method according to claim 8, wherein comparing the data via the quality control device includes comparing machine adaptable data with the requisition data as well as comparing the geometry characterizing data with the requisition data.

19. In a stock removal workshop for the production of a dental product, including a dental restoration product, the stock removal workshop having at least one stock removal machine operable to remove stock material from a blank such that there remains a dental product having a finished geometry requisitioned by a selected one of a dental practice and a dental laboratory, and a stock removal plotter for controlling the stock removal machine operation and operable to convert requisition data received from the selected one of the dental practice and the dental laboratory which characterizes a desired geometry of the requisitioned dental product into control data for controlling the stock removal machine operation and further operable to receive data characterizing the finished geometry of the produced dental product generated via a geometry following operation in which the geometry of the produced dental product is followed via a selected one of scanning the produced dental product and non-scanning following of the finished geometry of the produced dental product, a quality control device comprising:

means for monitoring a quality control characteristic with respect to the produced dental product, wherein the dental product is still retained in its stock removal position at the stock removal machine; and a comparison device for comparing finished geometry characterizing data, generated indirectly by the stock removal plotter, relating to the produced dental product with the requisition data characterizing the desired geometry of the requisitioned dental product to determine deviations therebetween.

* * * * *